United States Patent
Christensen et al.

(10) Patent No.: US 8,088,900 B2
(45) Date of Patent: Jan. 3, 2012

(54) TWO-PHASE PRECIPITATION OF PROTEINS

(75) Inventors: Thorkild Christensen, Allerød (DK); Jan Anton Enoksen, Kokkedal (DK)

(73) Assignee: Novo Nordisk A/S, Bagsvaerd (DK)

( * ) Notice: Subject to any disclaimer, the term of this patent is extended or adjusted under 35 U.S.C. 154(b) by 198 days.

(21) Appl. No.: 12/294,278

(22) PCT Filed: Mar. 28, 2007

(86) PCT No.: PCT/EP2007/052976
§ 371 (c)(1),
(2), (4) Date: Sep. 24, 2008

(87) PCT Pub. No.: WO2007/113188
PCT Pub. Date: Oct. 11, 2007

(65) Prior Publication Data
US 2009/0286966 A1    Nov. 19, 2009

Related U.S. Application Data

(60) Provisional application No. 60/744,067, filed on Mar. 31, 2006.

(30) Foreign Application Priority Data

Mar. 30, 2006 (EP) .................................. 06111966

(51) Int. Cl.
C07K 14/00 (2006.01)
C07K 17/00 (2006.01)
C07K 16/00 (2006.01)
A23J 1/00 (2006.01)

(52) U.S. Cl. ........ 530/419; 530/412; 530/418; 530/422; 530/424

(58) Field of Classification Search .................. None
See application file for complete search history.

(56) References Cited

U.S. PATENT DOCUMENTS

| | | | |
|---|---|---|---|
| 5,304,310 A | 4/1994 | Lang et al. | |
| 5,728,559 A | 3/1998 | Nilsson et al. | |
| 6,566,329 B1 * | 5/2003 | Meyn et al. | 514/12 |
| 7,332,289 B2 * | 2/2008 | Takeda et al. | 435/7.1 |
| 2009/0286966 A1 * | 11/2009 | Christensen et al. | 530/419 |

FOREIGN PATENT DOCUMENTS

| | | | |
|---|---|---|---|
| EP | 747391 | | 12/1996 |
| EP | 1561756 | | 8/2005 |
| EP | 1707634 | * | 10/2006 |
| EP | 2004671 A1 | * | 12/2008 |
| WO | WO91/10677 | | 7/1991 |
| WO | WO97/34919 | | 9/1997 |
| WO | WO 2007/113188 A1 | * | 10/2007 |

OTHER PUBLICATIONS

Flanagan et al, Biomedical Chromatography, 2006, 20:530-538.*
Chia Kai Su et al, Process Biochemistry, 2006, vol. 41, No. 2, pp. 257-263.
Dennison, Clive et al, Protein Expression and Purification, 1997, vol. 11, No. 2, pp. 149-161.
Paulie, B.J.A et al, Protein Expression and Purification, 2004, vol. 34, No. 2, pp. 311-316.
Leonil et al, Enzyme and Microbial Technology, 1994, vol. 16, No. 7, pp. 591-595.
Fransson et al, Pharmaceutical Research, 1997, vol. 14, No. 5, pp. 606-612.

* cited by examiner

*Primary Examiner* — Nita M Minnifield
(74) *Attorney, Agent, or Firm* — Teresa Chen

(57) ABSTRACT

Provided are new methods for precipitating proteins comprising (a) providing a protein solution, (b) adding a salt to the solution, (c) either (i) adjusting pH of the composition to below the pI of the protein (in cases where the method is directed towards precipitation of most or all proteins in the solution) or (ii) adjusting the pH of the composition to above the pI of the protein (in cases where keeping the target protein in solution is desired), and (d) adding an organic compound to the solution, wherein (I) in the case where the method comprises step (c)(i) a two phase solution is formed wherein at least about 75% of the protein is contained in the protein phase or (II) in the case where the method comprises step (c)(ii) the method further comprises removing precipitated impurities from the protein solution.

33 Claims, 4 Drawing Sheets

TWO-PHASE PRECIPITATION OF PROTEINS

CROSS-REFERENCE TO RELATED APPLICATIONS

This application is a 35 U.S.C. §371 national stage application of International Patent Application PCT/EP2007/052976 (published as WO 2007/113188), filed Mar. 28, 2007, which claimed priority of European Patent Application 06111966.5, filed Mar. 30, 2006; this application further claims priority under 35 U.S.C. §119 of U.S. Provisional Application 60/744,067, filed Mar. 31, 2006.

FIELD OF THE INVENTION

The various aspects of the invention described herein primarily relate to new methods for precipitating proteins.

BACKGROUND OF THE INVENTION

Precipitation is a widely used method for the recovery of proteins from various solutions. Proteins in solution vary greatly in their solubility depending on their amino acid composition and the characteristics of the solvent (such as ionic strength and temperature). A number of methods for precipitation of proteins are well known. Protein crystallization, for example, is frequently used to precipitate proteins, but this method requires typically comprehensive development to achieve right crystallization conditions.

Isoprecipitation is another frequently used protein precipitation method, making use of the fact that a proteins solubility has a minimum at the protein's isoelectric point (PI). However, due to posttranslational modifications a number of proteins do not have a well defined PI. For example, coagulation factor VII ("FVII" or "FVIIa" (when referring to the activated form of FVII)) comprises y-carboxy groups and sialic acid groups, but not in any fixed number, making the pI of FVII difficult to define.

Protein precipitation also frequently is induced by addition of an organic solvent, to alter the nature of the solution in which the protein is contained. Traditionally, it has been believed that if there is a significant decrease in the dielectric constant of the medium with the addition of an organic solvent, the solubility of any proteins in a solution should also decrease and proteins should precipitate. More recent research has suggested that dehydration of protein surfaces is a reason (if not the reason) for precipitation of proteins in the presence of organic solvents.

"Salting out" protein precipitation methods have been used extensively, particularly before the development of more recently developed chromatographic purification methods. Salting out of proteins makes use of the fact that a protein's solubility often decreases at high salt concentrations (and proteins can therefore be made to precipitate under such conditions). Various salts have different salting out effects, but the general principles for salting out are presented in the so-called Hofmeister series that have been known for more than 100 years. Besides the particular salt used, the nature of the protein in question also influences its ability to be precipitated by such a method. Ammonium sulphate is among the salts that most often has been used for precipitation of proteins.

The methods of salting out precipitation, organic solvent precipitation, and isoprecipitation, have frequently been used in isolation, rather than in combination with each other.

One method that makes use of a high salt concentration (typically using ammonium sulphate in an order 0.3-5 M) in combination with a water soluble organic solvent (typically t-butanol) is described in the so-called Three Phase Partitioning (TPP). t-butanol is regarded as completely miscible with water, but at high salt concentrations a two phase system occurs, the lower phase is the aqueous salt phase and the upper is t-butanol phase. However, if protein is present in such a system, a third phase develops in the boundary between the two above-mentioned phases as precipitated protein. Large amounts of t-butanol (17-33%) or other organic substance are required (relative to the aqueous phase) in such a method (see, e.g., C. Dennison et al., Protein Expression and Purification 11, 149-161 (1997), which discloses a so-called Three Phase Partitioning (TPP) system, a system wherein two liquid phases are formed, and where proteins partion between the liquid phases, resulting in a third solid phase in the boundary between the two liquid phases). The combination ammonium sulphate and t-butanol are far the most used, in such methods, however others salts and other organic compounds (such as n-butanol) have also been tried.

J. Leonil et al., Enzyme Microb. Technol. 16, 591-595 (1994), describes precipitation of peptides from a tryptic digest of casein using NaCl and ammonium sulphate. The authors found that particularly pH influenced precipitation and in particular low pH values were preferable. However, no organic compounds were used in the precipitation method.

Solvent effects on solubility and stability of IGF-1 also have been studied (J. Fransson et al., Pharmaceutical Research 14, 606-612 (1997)). The goal of this work was to investigate circumstances in which a stable protein solution could be obtained without negatively impacting IGF-1's tertiary structure. The report mentions that IGF-1 precipitates in 145 mM NaCl and 140 mM benzyl alcohol (benzyl alcohol is a commonly used preservative known to have a tendency to promote protein precipitation). However, the work of Franson et al. related to formulation and stabilisation of IGF-1, rather than methods for protein precipitation, such that the amount of protein precipitated was small (being an unintended effect).

Su et al, Process Biochemistry 41(2), 257-263 (2006) describes a so-called aqueous two-phase system for separation of proteins, which two-phase system can be brought about by mixing polyethylene glycol and a salt in water and wherein both phases are liquid. Such systems tend to form two liquid phases. If a mixture of proteins are present they will partion unequally between the two aqueous phases, giving rise to a separation of the proteins.

U.S. Pat. No. 5,728,559 discloses the isolation of proteins and in particular enzymes from aqueous solutions by crystallization by addition of a salt at a concentration of 1.5 M or below, but without any pH adjustments, followed by addition of a water soluble polymer resulting in a crystalline product after stirring. The polymer is typically a glycol such as polyethylene glycol.

EP0474391 discloses a method in which an acylated protein (insulin) may be isolated by adjusting the pH to a value near the pI of the protein. Then a suitable amount of an alcohol is added. In the example ethanol is used in an amount of 0.46 liter per liter solution to give a precipitation, in fact a so-called isoprecipitation is described. No salt is added.

EP1561756 discloses the removal of impurities like DNA and viruses from a protein solution (particularly antibodies). This is done by lowering the pH to a value equal to or lower than the pI of the protein with low conductivity. Under these conditions impurities as particles may be removed, while the protein of interest remains in solution. No organic solvent is used.

There remains a need for alternative and improved methods for precipitating proteins. The present invention described herein provides such methods. These and other advantages and features of the invention are further described in the description of the invention provided herein.

SUMMARY OF THE INVENTION

DESCRIPTION OF THE INVENTION

Figure 1:
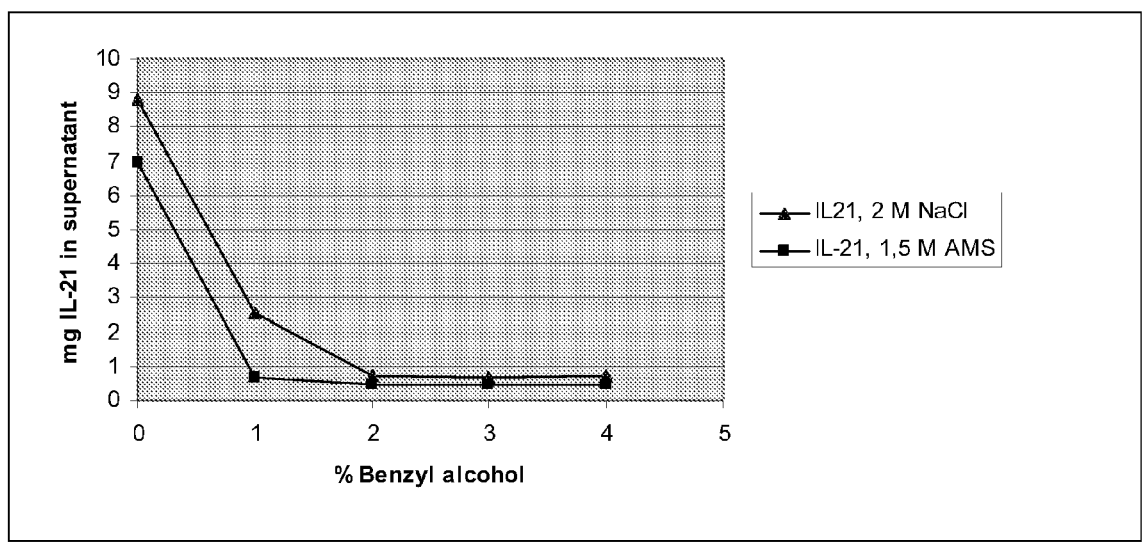
FIG. 1 illustrates the results obtained in precipitating IL21 in NaCl or (NH4)2SO4 with benzyl alcohol according to one aspect of the invention.

The invention described herein provides a method of precipitating a protein comprising (a) providing a protein solution, (b) adding a salt to the solution, (c) adjusting pH of the composition to below the pI of the protein, and (d) adding an organic compound to the solution, so as to form a two-phase system, wherein the protein is precipitated in a solid protein phase, which may then for instance be separated from the liquid phase by filtration.

A protein solution can be provided by any suitable means and the inventive method can be practiced with any suitable type of protein solution. A protein solution can be, for example, the product of recombinant protein expression; a biological sample taken from an organism; or a solution containing a protein produced by chemical synthesis methods. A protein solution may also be provided as purification product of such a medium, such as a fraction from a chromatography purification step.

The term "protein" is used herein as referring to peptides (single chain amino acid polymers of about 3-50, typically about 3-40 amino acid residues in length) as well as polypeptides (single chain amino acid polymers of 50 and more amino acid residues) and more complicated (e.g., multi-chain) proteins.

The protein solution can include any number of proteins of interest and/or undesirable ("contaminating") proteins. Thus, for example, the solution may include one, two, three, or more proteins of interest.

In one aspect, the target protein is a protein that is subjected to one or more variable posttranslational modifications, that cause the protein to be associated with a poorly defined PI. As mentioned above coagulation factor VII proteins (and analogues or derivatives of such proteins having similar features in terms of posttranslational modifications) are an example of such a protein.

Other examples of proteins that the method can be advantageously applied to include growth hormone proteins (GHs) and interleukins ("ILs"), such as IL-2, IL-20, and IL-21. Other proteins of interest may include insulins; glucagon-like proteins (e.g., GLP-1 or GLP-2); other coagulation factors (e.g., factor VIII, factor IX, factor XI, or factor XIII); erythropoietin; vascular endothelial growth factors (VEGFs); interferons (e.g., IFN-α, IFN-β, or IFN-γ), colony stimulating factors (e.g., G-CSF); soluble receptor proteins (e.g., soluble TNFα receptor proteins); tissue plasminogen activator (tPA); antibodies; IGF-1; fibroblast growth factor (FGF); and analogues of such proteins, derivatives of such proteins, and fusion proteins related to such proteins (e.g., albumin-interferon fusion proteins).

In one embodiment, at least about 75% of the protein is precipitated in the solid protein phase.

In one embodiment, the two-phase system contains a solid protein phase and no more than one liquid phase.

The salt added to the solution can be any suitable salt. Suitability in the context of the inventive method means that the salt is capable to induce the effects necessary, in combination with the other steps of the method, to achieve a suitable level of precipitation with respect to the protein(s) of interest (or "target proteins," which may be, e.g., the entire protein content of the composition). Suitability also typically means that the salt does not include any ions that may be detrimental to the health of someone receiving a protein solution comprising the salt, such as wherein the method is applied to concentrate a protein for purposes of generating a pharmaceutical composition.

The salt added to the solution typically is a so-called "salting-out" salt. Examples of salting out salts include sulphate salts, chloride salts, nitrate salts, phosphate salts, citrate salts, and thiocyanate salts. Specific examples of suitable salts are known in the art. In another aspect, the salt is a "salting-in" salt. Additional examples of suitable "salting-in" salts are known.

Typically, the salt is selected from NaCl or ammonium sulfate. Ammonium sulfate, is very soluble, allowing for a range of concentrations to be applied to precipitate a variety of proteins under different conditions (which is particularly advantageous in other aspects of the invention wherein precipitation of the target protein is not desired). For this and other reasons, ammonium sulfate is typically an advantageous salt in the practice of the inventive methods described herein. Other suitable salts include ammonium acetate, citric acid salts, and tartaric acid salts.

The salt can be added in any suitable concentration. Suitability with respect to concentration also refers to effectively obtaining precipitation of the desired protein product or achieving other desired effect. The ordinarily skilled artisan will recognize that different proteins may become less soluble (tends towards "salting out") under different conditions, such that the amount of salt that will be most effective will vary (but the appropriate amount can be readily determined using routine experimentation). An advantage of the method is that the amount of salt used in the precipitation process typically is significantly less than an amount used in a traditional "salting out" precipitation (thereby, among other things, resulting in less risk of protein denaturation or less amounts of undesirable denatured protein products than obtained in such methods). Typically, the final salt concentration achieved in step (a) of the method is in the order of about 0.1 to about 3 M (e.g., about 0.2 M to about 2 M, about 0.05M to about 1 M, for example about 0.2-0.8 about M, such as 0.2-0.6 about M, such as about 0.2-0.4 M, e.g., about 0.25 M).

After the salt addition phase, the pH of the composition is lowered to some suitable amount below the pI of the protein. The lowering of the solution can be achieved by any suitable method. Typically an acid, such as sulfuric acid, is added to the solution so as to lower the pH to the desired level. As with other steps of the method, suitability is associated with the desired precipitation effect. In general, the pH obtained in this step should be about 0.5 to about 5 pH units below the protein's PI, such as about 1-4 units below the protein's PI, such as about 1.5-3.5 units below the protein's PI, for example about 2 units below the protein's PI.

In the next step, a small amount (e.g., a few percent) of a suitable organic solvent is added to the solution as the final step towards inducing precipitation of the proteins to be precipitated. In one embodiment, the organic compound is water soluble. In one embodiment, the organic compound is hydrophobic and water soluble. Examples of such solvents include benzyl alcohol, n-butanol, and benzoic acid. In general, phenol and phenol derivatives may be suitable. Benzyl alcohol has been found to be particularly advantageous in the practice of the method. In one aspect, the organic compound is t-butanol. However, in another aspect, the organic compound is defined as not being t-butanol. In one embodiment, the water soluble organic solvent is not a polymer.

Addition of a water soluble organic solvent in small amount does not result in the formation of two liquid phases and consequently, the water soluble organic solvent is added in an amount which does not induce the formation of two liquid phases, on the contrary, one liquid and one solid phase will form. In one embodiment, the organic solvent is added in an amount, which between 0.5% and 5% of the resulting solution In one embodiment, the organic solvent is added in an amount, which is not more than about 5%, such as about 5% of the resulting solution. In one embodiment, the organic solvent is added in an amount, which is not more than about 4%, such as about 4% of the resulting solution. In one embodiment, the organic solvent is added in an amount, which is not more than about 3%, such as about 3% of the resulting solution. In one embodiment, the organic solvent is added in an amount, which is not more than about 2%, such as about 2% of the resulting solution. In one embodiment, the organic solvent is added in an amount, which is not more than about 1%, such as about 1% of the resulting solution.

In an advantageous aspect, the organic solvent that is selected has a protein preservative effect. For example, benzyl alcohol and benzoic acid are both known to be preservatives. Thus, besides further inducing precipitation of the target protein(s), the precipitated protein product also is protected against undesirable microbial growth.

The amount of organic solvent used in generally low (less than about 10%, and typically only a few percent). The amount may be, e.g., about 0.25 to about 4%, such as about 0.5 to about 3%, such as about 0.75-2.5%, for example about 1% to about 2%. These amounts are significantly less than used in, e.g., a TPP method.

Typically, during the entire process the protein solution is gently stirred. In contrast to methods that rely on crystallization or other forms of precipitation, the method can generally be practiced at room temperature conditions.

The addition of the organic solvent creates a protein-rich solid phase and a protein-poor phase in the solution. The two phase system lends itself well to further purification of the protein by conventional methods, such as filtration and/or centrifugation techniques.

By practice of such a method, precipitation of at least about 65%, such as at least about 75% of a target protein can be readily obtained. Advantageously, as illustrated by some of the exemplary experiments provided herein, target protein precipitation yields as high as about 80% or more, about 85% or more, about 90% or more, or even 95% or more (e.g., nearly 100% or 100% (within means of detection)) may be achieved.

The precipitated product may be kept in solution for considerable lengths of time advantageously in association with the prevention of certain types of degradation often associated with proteins in solution, such as dimerization, polymerization, or generation of desamido forms. Proteins in solid form may resist such processes and otherwise be more stable than proteins in solution. Precipitated proteins also may be able to better retain proper tertiary structure over lengths of time. Thus, one aspect of the invention involves the generation of a precipitated protein product and the use of that product as an intermediate for the later generation of a purified protein solution. In another aspect, the intermediate or purified product is subjected to freezing or freeze-drying. In any event, the precipitation step also can serve as a method of concentrating protein(s) in the solution or target proteins in the solution (either by precipitation of such proteins or, in the aspects described below by retaining such proteins in solution while precipitating "contaminating" (undesirable) protein species in the protein solution). In other words, the method can serve as a method of concentrating a protein.

As already suggested by various preceding passages, in another aspect, the invention provides a method of purifying a protein solution comprising (a) providing a protein solution, (b) adding a salt to the solution, (c) adjusting pH of the composition to above the pI of the protein, and (d) adding an organic compound to the solution so as to obtain precipitation of protein impurities from the solution, and removing precipitated protein impurities from the protein solution. The basic difference in the method of this aspect is that the conditions used are such that complete protein precipitation is avoided and that precipitation of undesirable proteins is obtained while desirable protein(s) are kept in solution. This can be accomplished by, e.g., modifying the amount of ammonium sulphate used in the salt addition step of the method. For example, below 25% ammonium sulphate saturation, particulate or high molecular weight (MW) proteins precipitate. Further sequential "cuts" can also be obtained by increasing the concentration in 10-20% incremental steps until proteins that are desired to be precipitated are precipitated—where total precipitation is desired an amount such as about 80-90% can be used. The salt and pH adjustment steps also can be modified to retain desirable proteins in solution—such as, e.g., not reducing the pH significantly below the pI of target proteins. The method of this aspect, generally, can be used to purify solutions containing proteins of interest, such as, e.g., where the target protein is a recombinant product (e.g., hGH, FVII, FXIII, FXI, an insulin, etc.) and the initial protein solution is a lysate from a recombinant cell that expressed that product (e.g., a recombinant hGH-expressing bacterial cell lysate) or other type of complex protein mixture (e.g., a biological sample comprising many types of proteins in addition to the target protein). In one aspect, the pH may be increased to above the target protein's PI, and the other steps performed so as to remove impurities while keeping the target protein in solution. In this sense, this second aspect method (wherein the target protein is kept in solution) may be combined with the first aspect (wherein the target protein is precipitated) as a combined method for removing undesirable proteins and concentrating desired ones.

The various methods of the invention can be combined with other protein purification methods such as chromatographic purification, filtration, etc. Alternatively, the practice of the methods can be characterized as lacking the performance of these or other steps (e.g., in one aspect, the method is characterized by the lack of a crystallization step, the lack of any precipitation-inducing polymer, etc.). In one aspect, the solution is free of mannitol or other agents that may be found in a final protein solution.

EXPERIMENTAL METHODS AND DATA

The following exemplary experimental methods and data are presented to better illustrate various aspects of the invention, and related illustrative enabling technology, but in no event should be viewed as limiting the scope of the invention.

Example 1

Precipitation of IL-21 in NaCl and $(NH_4)_2SO_4$ with Benzyl Alcohol

Starting Material: IL21 solution with a concentration of 2.3 mg/ml and benzyl alcohol (Bzl-OH). Solutions of 5 M NaCl and 3 M $(NH_4)_2SO_4$ (AMS) were made.

The following mixtures were prepared as shown in Schema 1 and 2:

| | Schema 1 | | | |
|---|---|---|---|---|
| | ml IL21 | ml 5 M NaCl | µl Bzl-OH | % Bzl-OH |
| 1 | 5 | 3.4 | 0 | 0 |
| 2 | 5 | 3.4 | 85 | 1 |
| 3 | 5 | 3.4 | 170 | 2 |
| 4 | 5 | 3.4 | 255 | 3 |
| 5 | 5 | 3.4 | 340 | 4 |

Thus, the concentration in the IL21 mixtures was approximately 1.3 mg IL21/ml in 2 M NaCl and the concentration of benzyl alcohol varied from 0-4%. The mixtures were prepared and left for a short while followed by filtration. UV absorption of the supernatants was measured at $A^{280}$ and the absorbance measurements converted to total amount of mg in the supernatants. The result is shown in FIG. 1—upper curve.

| | Schema 2 | | | |
|---|---|---|---|---|
| | ml IL21 | ml 3 M AMS | µl Bzl-OH | % Bzl-OH |
| 1 | 5 | 5 | 0 | 0 |
| 2 | 5 | 5 | 100 | 1 |
| 3 | 5 | 5 | 200 | 2 |
| 4 | 5 | 5 | 300 | 3 |
| 5 | 5 | 5 | 400 | 4 |

The concentration in the mixtures of IL21 here was 1.1 mg IL21/ml in 1.5 M AMS and benzyl alcohol content varied from 0-4%. The mixtures were prepared and left for a short while followed by filtration. UV absorption of the supernatants was measured at $A^{280}$ and the absorbance measurements converted to total amount of mg in the supernatants. The result is shown in FIG. 1—lower curve.

From the figure it is seen that with a benzyl alcohol concentration of approximately 1-2% (v/v) about 92-93% of IL21 was precipitated.

Example 2

Precipitation Experiment with hGH Above its pI 52.4 mg solid hGH was dissolved in 26.2 ml water at a pH of 7-7.5 (i.e. above hGH's pI of 4.9). The concentration of hGH became 2 mg/ml. Solutions of 0.5 M NaCl and 0.5 M AMS were prepared. The following was mixed as shown in Schema 3.

| | Schema 3 | | | |
|---|---|---|---|---|
| | ml hGH | ml 0.5 M NaCl or AMS | µl Bzl-OH | % Bzl-OH |
| 1 | 2 | 2 | 0 | 0 |
| 2 | 2 | 2 | 20 | 0.5 |
| 3 | 2 | 2 | 30 | 0.75 |
| 4 | 2 | 2 | 40 | 1 |
| 5 | 2 | 2 | 80 | 2 |

After standing and filtration UV measurements were carried out and $A^{280}$ measured, it turned out that the entire amount of hGH was present in the filtrates and hGH was not precipitated.

Example 3

Precipitation Experiment with hGH Below its pI 43 mg solid hGH was dissolved in 21.5 ml water at pH 4. The concentration in the hGH sample was approximately 2 mg/ml. Apart from pH, mixtures were prepared as shown in Example 2. Likewise, the concentrations in the supernatants were determined. The results are shown in FIG. 2.

Figure 2:
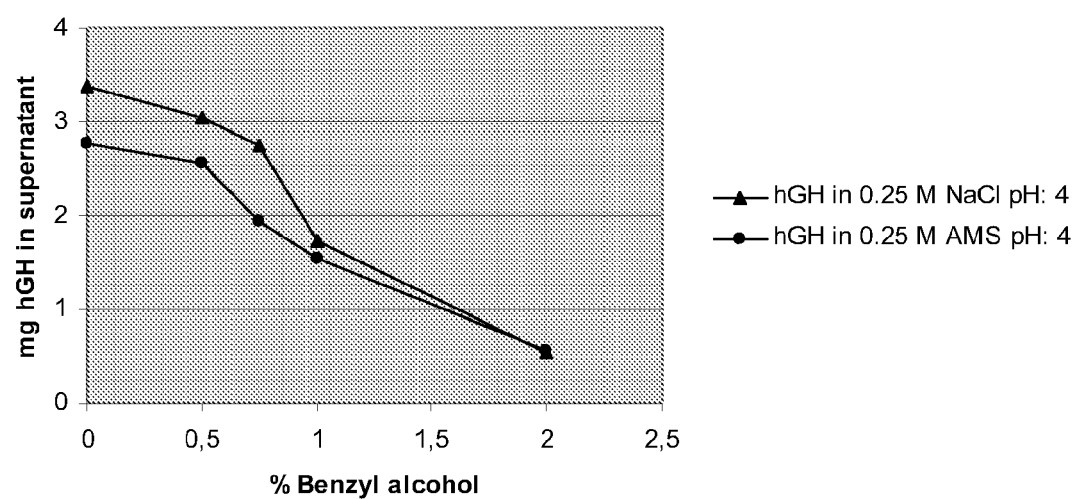
FIG. 2 illustrates the results obtained in precipitating hGH in NaCl or ammonium sulphate buffers according to another aspect of the invention.

From FIG. 2 it is seen that with a benzyl alcohol concentration of about 2% (v/v) approximately 75% hGH was precipitated. It has to be noted that salt concentration of only 0.25 M was used. Higher salt concentrations are expected to result in even more effective precipitation.

Example 4

Precipitation of FVIIa with Benzyl Alcohol at Different pH Values

As FVIIa is subject to post translational modifications—i.e., both A-carboxylated and glycosylated also with sialic acid residues, it does not have a well defined pI (rather FVIIa can be characterized in association with a pI range). However, the modifications will lower pI as compared with an unmodified form of the protein.

A solution with a content of 1.39 mg FVIIa/ml was used at pH values of 4 and 8. A 2 M AMS was also prepared both at pH 4 and 8. The following was mixed as shown in Schema 4.

| | Schema 4 | | | | |
|---|---|---|---|---|---|
| | µl FVIIa | Water µl | 2 M AMS µl | µl Bzl-OH | % Bzl-OH |
| 1 | 720 | 280 | 1000 | 0 | 0 |
| 2 | 720 | 280 | 1000 | 10 | 0.5 |
| 3 | 720 | 280 | 1000 | 15 | 0.75 |
| 4 | 720 | 280 | 1000 | 20 | 1 |
| 5 | 720 | 280 | 1000 | 40 | 2 |

After standing and filtration the content of FVIIa present in the supernatant was determined by measuring $A^{280}$ and conversion to total amount of FVIIa. The results are shown in FIG. 3.

Figure 3:
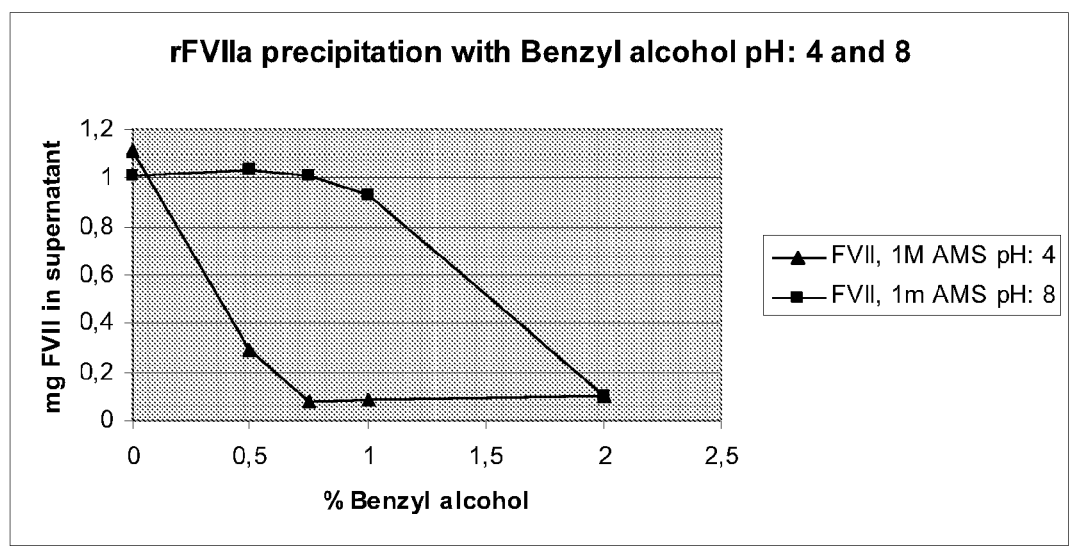
FIG. 3 illustrates the results obtained in precipitating rFVIIa according to another aspect of the invention.

From FIG. 3 it is seen that at pH 4 approximately 90% of FVIIa is precipitated in the presence of only about 0.75% benzyl alcohol. At pH 8, no FVIIa is precipitated with a benzyl alcohol concentration of 0.75%. However, a content of 2% benzyl alcohol precipitates also about 90% FVIIa at pH8, similar to the precipitation at pH 4.

Example 5

Precipitation with N-butanol and Isobutanol in NaCl and AMS Solutions

An IL21 solution with a content of 2.3 mg/ml, 5 M NaCl and 3 M AMS solutions were prepared and mixed as shown in Schema 5 and 6.

Schema 5

| | ml IL21 | ml 5 M NaCl | µl Butanol | % Butanol |
|---|---|---|---|---|
| 1 | 5 | 3.4 | 85 | 1 |
| 2 | 5 | 3.4 | 170 | 2 |
| 3 | 5 | 3.4 | 255 | 3 |
| 4 | 5 | 3.4 | 340 | 4 |

Schema 6

| | ml IL21 | ml 3 M AMS | µl Butanol | % Butanol |
|---|---|---|---|---|
| 1 | 5 | 5 | 100 | 1 |
| 2 | 5 | 5 | 200 | 2 |
| 3 | 5 | 5 | 300 | 3 |
| 4 | 5 | 5 | 400 | 4 |

After standing and filtration the content of IL21 in the supernatants were determined by measuring $A^{280}$. The results are shown in FIG. 4.

Figure 4:
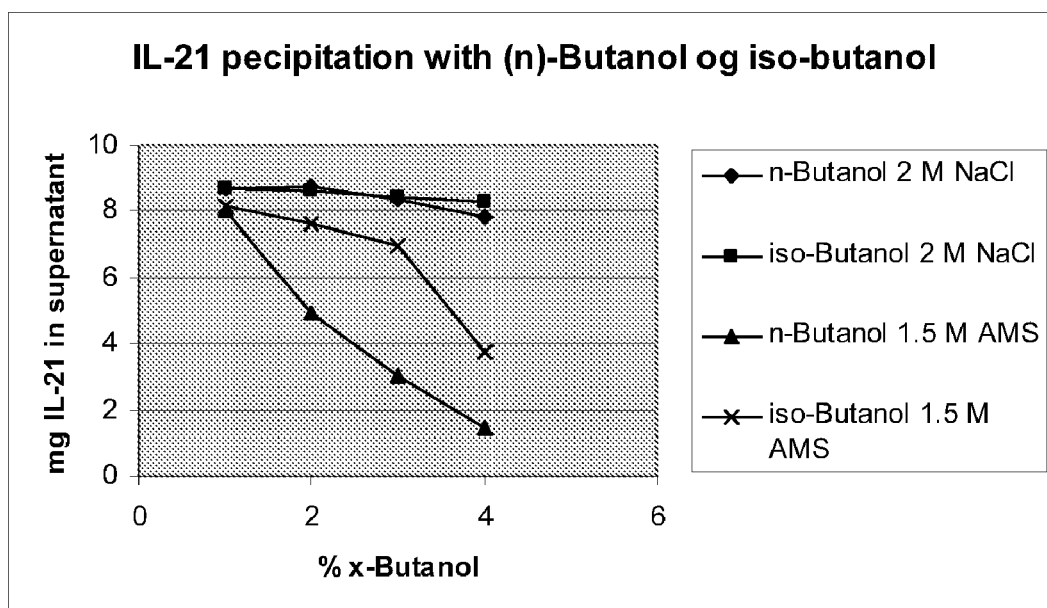
FIG. 4 illustrates the results obtained in precipitating interleukin-21 with butanols according to another aspect of the invention.

From FIG. 4 it can be seen that IL21 is not precipitated with butanol in NaCl solutions. However, in 1.5 M AMS IL21 is precipitated. With 4% n-butanol about 83% IL21 is precipitated and about 60% with iso-butanol.

Example 6

Precipitation with Benzoate

Starting material IL21 with a concentration of 2.3 mg/ml, 3 M AMS, 5 M NaCl, and solid sodium benzoate.

The following mixtures were prepared as shown in Schema 7. As benzoate absorbs UV light it is not possible to determine the amount of protein in solution by determination of $A^{280}$. Therefore, a visual estimation was used.

Schema 7

| | Ml IL21 | Salt | Sodium benzoate | Visual inspection |
|---|---|---|---|---|
| 1 | 5 | 5 ml AMS | 100 mg | Very weak precipitation |
| 2 | 5 | 5 ml AMS | 300 mg | Strong precipitation |
| 3 | 5 | 3.4 ml NaCl | 200 mg | Very weak precipitation |
| 4 | 5 | 3.4 ml NaCl | 400 mg | Some precipitation |

From Schema 7 it is seen that an organic entity such as benzoate can promote precipitation. 300 mg sodium benzoate in 10 ml will give a concentration of approximately 20 mM.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention (e.g., "a protein"; "a salt", etc.) are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate) and visa versa.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method of precipitating a protein comprising (a) providing a protein solution, (b) adding a salt to the solution, (c) adjusting pH of the solution of (b) to below the pI of the protein, and (d) adding an organic compound to the solution, so as to form a two-phase system, wherein the two-phase system contains a solid protein phase and no more than one liquid phase, and wherein the protein is precipitated in the solid protein phase.

2. A method according to claim 1, wherein at least about 75% of the protein is precipitated in the solid protein phase.

3. A method according to claim 1, wherein the organic compound is water soluble.

4. A method according to claim 3, wherein the organic compound is hydrophobic and water soluble.

5. A method according to claim 4, wherein the organic compound is selected from benzyl alcohol, n-butanol, benzoic acid, phenol, or a phenol derivative.

6. A method according to claim 5, wherein the organic compound is benzyl alcohol.

7. A method according to claim 1, wherein step (d) consists of increasing the concentration of the organic compound to from about 0.5% to about 5%.

8. A method according to claim 1, wherein step (d) consists of increasing the concentration of the organic compound to from about 1% to about 3%.

9. A method according to claim 1, wherein step (b) consists of increasing the salt concentration to a concentration of from about 0.1 M to about 3 M.

10. A method according to claim 9, wherein step (b) consists of increasing the salt concentration to a concentration of from about 0.1 M to about 1 M.

11. A method according to claim 10, wherein step (b) consists of increasing the salt concentration to about 0.25 M.

12. A method according to claim 1, wherein the pH obtained in step (c) is from about 0.5 to about 5 pH units below the protein's pI.

13. A method according to claim 12, wherein the pH obtained in step (c) is about 2 pH units below the protein's pI.

14. A method according to claim 1, wherein the salt is NaCl, ammonium sulphate, or a mixture thereof.

15. A method according to claim 14, wherein the salt is ammonium sulphate.

16. A method according to claim 1, wherein the protein is IL-21.

17. A method according to claim 1, wherein the protein is FVII.

18. A method of purifying a protein in a protein solution comprising (a) providing a protein solution, (b) adding a salt to the solution, (c) adjusting pH of the solution of (b) to above the pI of the protein, and (d) adding an organic compound to the solution so as to form a two-phase system, wherein the two-phase system contains a solid protein phase and no more than one liquid phase, and removing precipitated protein impurities from the protein solution.

19. A method according to claim 18, wherein at least about 75% of the protein is precipitated in the solid protein phase.

20. A method according to claim 18, wherein the organic compound is water soluble.

21. A method according to claim 20, wherein the organic compound is hydrophobic and water soluble.

22. A method according to claim 21, wherein the organic compound is selected from Benzyl alcohol, n-butanol, benzoic acid, phenol, or a phenol derivative.

23. A method according to claim 22, wherein the organic compound is benzyl alcohol.

24. A method according to claim 18, wherein step (d) consists of increasing the concentration of the organic compound to from about 0.5% to about 5%.

25. A method according to claim 18, wherein step (d) consists of increasing the concentration of the organic compound to from about 1% to about 3%.

26. A method according to claim 18, wherein step (b) consists of increasing the salt concentration to a concentration of from about 0.1 M to about 3 M.

27. A method according to claim 26, wherein step (b) consists of increasing the salt concentration to a concentration of from about 0.1 M to about 1 M.

28. A method according to claim 27, wherein step (b) consists of increasing the salt concentration to about 0.25 M.

29. A method according to claim 18, wherein the pH obtained in step (c) is from about 0.5 to about 5 pH units above the protein's pI.

30. A method according to claim 29, wherein the pH obtained in step (c) is about 2 pH units above the protein's pI.

31. A method according to claim 18, wherein the salt is NaCl, ammonium sulphate, or a mixture thereof.

32. A method according to claim 31, wherein the salt is ammonium sulphate.

33. A method according to claim 32, wherein the protein is hGH and the protein solution is a recombinant hGH-expressing bacterial cell lysate.

* * * * *